(12) United States Patent
Sadler et al.

(10) Patent No.: US 9,045,697 B2
(45) Date of Patent: Jun. 2, 2015

(54) DISTILLATION COLUMN HEAT PUMP WITH COMPRESSOR INLET SUPERHEATER

(75) Inventors: Clayton C. Sadler, Arlington Heights, IL (US); Xin X. Zhu, Long Grove, IL (US); Tokhanh N. Ngo, Glendale Heights, IL (US); David J. Shecterle, Arlington Heights, IL (US)

(73) Assignee: UOP LLC, Des Plaines, IL (US)

(*) Notice: Subject to any disclaimer, the term of this patent is extended or adjusted under 35 U.S.C. 154(b) by 605 days.

(21) Appl. No.: 13/411,830

(22) Filed: Mar. 5, 2012

(65) Prior Publication Data

US 2013/0227986 A1      Sep. 5, 2013

(51) Int. Cl.
| | |
|---|---|
| *C07C 7/04* | (2006.01) |
| *C10G 7/00* | (2006.01) |
| *B01D 3/32* | (2006.01) |
| *B01D 3/14* | (2006.01) |
| *B01D 3/42* | (2006.01) |
| *B01D 3/00* | (2006.01) |

(52) U.S. Cl.
CPC *C10G 7/00* (2013.01); *B01D 3/322* (2013.01); *B01D 3/14* (2013.01); *B01D 3/4205* (2013.01); *C07C 7/04* (2013.01); *B01D 3/007* (2013.01); *Y02B 30/52* (2013.01)

(58) Field of Classification Search
CPC ............ B01D 3/14; B01D 3/32; B01D 3/322; B01D 3/42; B01D 3/4205; C07C 7/04
USPC ................ 202/158, 161, 162; 203/26, 87, 98; 196/99, 100, 134, 139; 208/350, 353
See application file for complete search history.

(56) References Cited

U.S. PATENT DOCUMENTS

| | | | | |
|---|---|---|---|---|
| 4,336,046 | A | * | 6/1982 | Schorre et al. .................. 62/623 |
| 4,444,571 | A | * | 4/1984 | Matson ............................. 95/48 |
| 4,559,108 | A | | 12/1985 | Ahlberg |
| 4,615,769 | A | * | 10/1986 | Horigome et al. ................ 203/2 |
| 4,753,667 | A | | 6/1988 | O'Connell et al. |
| 4,773,968 | A | * | 9/1988 | O'Connell et al. ............. 203/26 |
| 5,386,075 | A | * | 1/1995 | Keil et al. ..................... 585/800 |
| 5,602,291 | A | * | 2/1997 | Minkkinen et al. ........... 585/738 |
| 7,842,847 | B2 | | 11/2010 | Panditrao et al. |
| 7,908,861 | B2 | | 3/2011 | Chino et al. |
| 7,981,256 | B2 | * | 7/2011 | Wegerer et al. ................ 203/26 |

OTHER PUBLICATIONS

Krajnc M; Glavic P, Energy integration of mechanical heat pumps with process fluid as working fluid, Chemical Engineering Research & Design ,v 70, n A4, p. 407-420, Jul. 1992; ISSN: 02638762; Publisher: Institution of Chemical Engineers.
Lynd L R; Grethlein H E, Distillation With Intermediate Heat Pumps and Optimal Sidestream Return, Aiche J., v 32, n 8, p. 1347-1359, Aug. 1986; ISSN: 00011541; Publisher: John Wiley and Sons.
Galstaun, L.S. et al., Heat Pumping pays out in C5/C6 isom plant, Oil & Gas Journal, Nov. 12, 1979, p. 223-226.

* cited by examiner

*Primary Examiner* — Nina Bhat
*Assistant Examiner* — Jonathan Miller

(57) ABSTRACT

Hydrocarbon distillation columns with heat pumps and methods of operating them are described. The overhead stream is compressed to increase temperature so that it can be used both to heat the reboiler and to superheat the overhead stream before it enters the heat pump compressor.

17 Claims, 3 Drawing Sheets

US 9,045,697 B2

DISTILLATION COLUMN HEAT PUMP WITH COMPRESSOR INLET SUPERHEATER

BACKGROUND OF THE INVENTION

The invention relates generally to distillation columns, and more particularly to methods of distillation and distillation columns having a heat pump with a reboiler and an inlet superheater.

The Penex™ process from UOP LLC is designed for the catalytic isomerization of pentane, hexane, and mixtures thereof. As shown in FIG. 1, feed 10 is sent to reactors 15 where reactions take place over a fixed catalyst bed in the presence of hydrogen and at operating conditions that promote isomerization and minimize hydrocracking. The reactor effluent 20 is sent to a product stabilizer 25. The stabilizer bottoms stream 30 can be separated into normal and isoparaffin components by fractionation in a de-isohexanizer column 35. The de-isohexanizer column 35 separates higher octane di-methyl butane $C_6$ isomers and lighter material into an overhead stream 40 and lower octane methyl-pentane $C_6$ isomers and heavier material into a bottoms stream 45. The de-isohexanizer column 35 typically has a side cut where a methyl-pentane rich stream 60 is withdrawn and recycled back to the reactor 10. The overhead stream 40 is condensed in condenser 65, and sent to receiver 70. The receiver outlet stream 75 is divided into a first portion 80 which is returned to the de-isohexanizer column 35 and a second portion 85 which is recovered.

A portion 50 of the bottoms stream 45 is sent to a reboiler 55 where it is heated and returned to the de-isohexanizer column 35. The de-isohexanizer reboiler 55 typically uses low pressure or medium pressure steam as a heat source, and it is one of the largest energy consumers in a naphtha complex. Reducing the steam consumption of the de-isohexanizer column would lower the energy cost of the overall process.

Heat pumps can be utilized economically in hydrocarbon distillation columns where the temperature difference between the overhead and the bottoms stream is low, e.g., less than about 27.7° C. (50° F.). Propane/propylene splitters are examples of columns in which heat pumps can be used economically. Such columns are described in U.S. Pat. Nos. 4,753,667, and 7,842,847, for example. Other examples of the use of heat pumps in separation processes are found in U.S. Pat. Nos. 4,336,046, 4,559,108, and 7,908,861.

However, the use of a heat pump in a column for separating $C_5$ and $C_6$ components is typically not economical because the higher temperature difference between the overhead stream and the bottoms stream (e.g., 38.9° C. (70° F.) or more) requires higher compression ratios in the heat pump compressor and therefore higher compression costs.

Furthermore, compression of the $C_5$ and $C_6$ overhead vapor stream results in partial condensation of the stream. In order to avoid this condensation, the overhead vapor stream must be superheated before it enters the heat pump compressor. Galstaun et al., Heat pumping pays out in $C_5/C_6$ isom plant, Oil & Gas Journal, Nov. 12, 1979, pp. 223-226, discusses the use of steam to preheat the vapor before it enters the compressor. The requirement for steam superheating further erodes the economics of the heat pump.

SUMMARY OF THE INVENTION

One aspect of the invention is a process for hydrocarbon distillation. The process includes providing a hydrocarbon feed stream to a fractionation zone at a first position. The hydrocarbon feed stream is fractionated into an overhead stream and a bottoms stream. A first portion of the overhead stream is heated to a temperature above a dew point temperature of the overhead stream, and the heated first overhead stream portion is compressed. A portion of a stream is removed from the fractionation zone at a second position below the first position. The removed stream portion is heated by indirectly contacting the removed stream portion with the compressed first overhead stream portion. The heated removed stream portion is returned to the fractionation zone at a third position above the second position and below the first position. The pressure of the compressed first overhead stream portion is reduced to form a reduced pressure overhead stream. A portion of the reduced pressure overhead stream is returned to the top of the fractionation zone. The first overhead stream portion is heated by indirectly contacting the first overhead stream portion with the compressed first overhead stream portion after indirectly contacting the removed stream portion with the compressed first overhead stream portion.

Another aspect of the invention is a distillation column and heat pump. In one embodiment, the distillation column and heat pump includes a distillation column having a feed inlet at a first position, an overhead outlet, and a bottoms outlet. There is a reboiler having an inlet and an outlet, the reboiler inlet in fluid communication with a second position below the first position, and the reboiler outlet being in fluid communication with a third position on the distillation column, the third position being above the second position and below the first position. A heat exchanger is in heat exchange communication with at least a portion of the distillation column overhead outlet. There is a compressor having a compressor inlet in fluid communication with at least the portion of the distillation column overhead outlet and a compressor outlet in heat exchange communication with the reboiler and the heat exchanger, and an expansion valve having an expansion valve inlet in fluid communication with the compressor outlet and an expansion valve outlet in fluid communication with an inlet at a position above the first position and below the overhead outlet.

DETAILED DESCRIPTION OF THE INVENTION

In one aspect of the invention, a heat pump is combined with a distillation column to recover overhead condensing heat. The column includes a reboiler. The compressed overhead stream is used both to heat the reboiler and to superheat the overhead stream before it enters the heat pump compressor. By distillation column, we mean columns for separating two or more components.

In one embodiment, a side reboiler is used to reduce the bottoms reboiler duty while also reducing the overhead-side reboiler temperature difference and the required heat pump compressor compression ratio. The side reboiler is located between the overhead and the bottoms. If a side draw is used, the return from the side reboiler is below the side draw, e.g., about 4 theoretical trays below the side draw.

The side reboiler desirably uses high flux tubes to reduce the heat exchanger area and possibly the number of heat exchanger shells while maintaining a low temperature difference of less than about 16.7° C. (30° F.) between the overhead stream after compression and the stream removed from the column before reheating in the side reboiler. Low temperature differences will reduce the heat pump compressor requirements.

Furthermore, the hot side outlet for the side reboiler was found to have sufficient heat remaining after heating the side stream to superheat the overhead stream for the heat pump compressor inlet. This eliminates the external steam requirement for this exchanger, and significantly improves the economics of the process. A small steam heated superheater may be used to provide supplemental heat during start-up, if desired.

As will be understood by those of skill in the art, this design is not limited to use with de-isohexanizer columns. It can be used in any hydrocarbon distillation column which has a similar temperature difference between the overhead and bottoms streams (e.g., 38.9° C. (70° F.) or more). Suitable hydrocarbons include, but are not limited to, light hydrocarbons, such as $C_4$ to $C_7$ hydrocarbons. For example, the design can be used with a $C_5$ to $C_7$ feed. It can also be used to separate $C_4$ hydrocarbons (i.e., normal butane and isobutane) in a deisobutanizer column. The design can also be used with distillation columns which have a lower temperature difference between the overhead and bottoms stream, but which need superheating of the overhead stream to prevent condensation during compression. For example, it could be used with a narrower boiling range light hydrocarbon feed (e.g., $C_5$ to $C_6$ hydrocarbons with little to no $C_7$ hydrocarbons) without the side stream reboiler, as described below.

Figure 1:
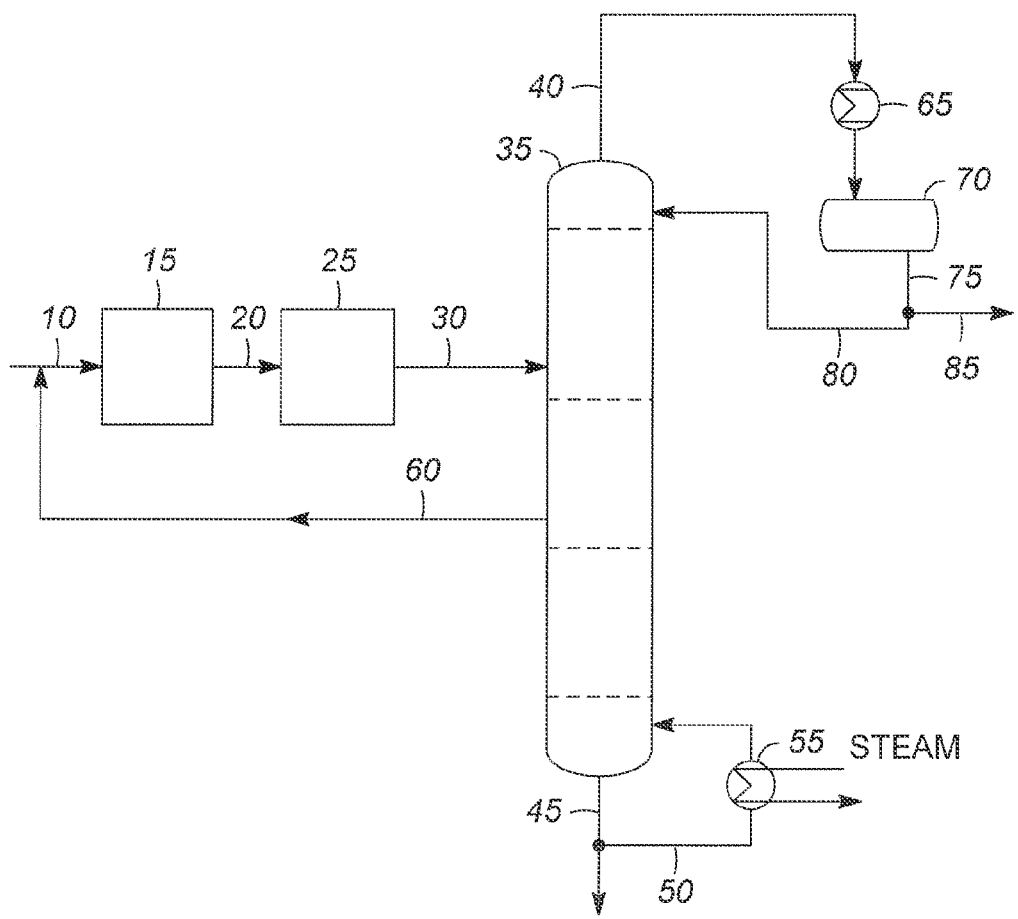
FIG. 1 is a schematic of a current separation unit with a de-isohexanizer column.
Figure 2:
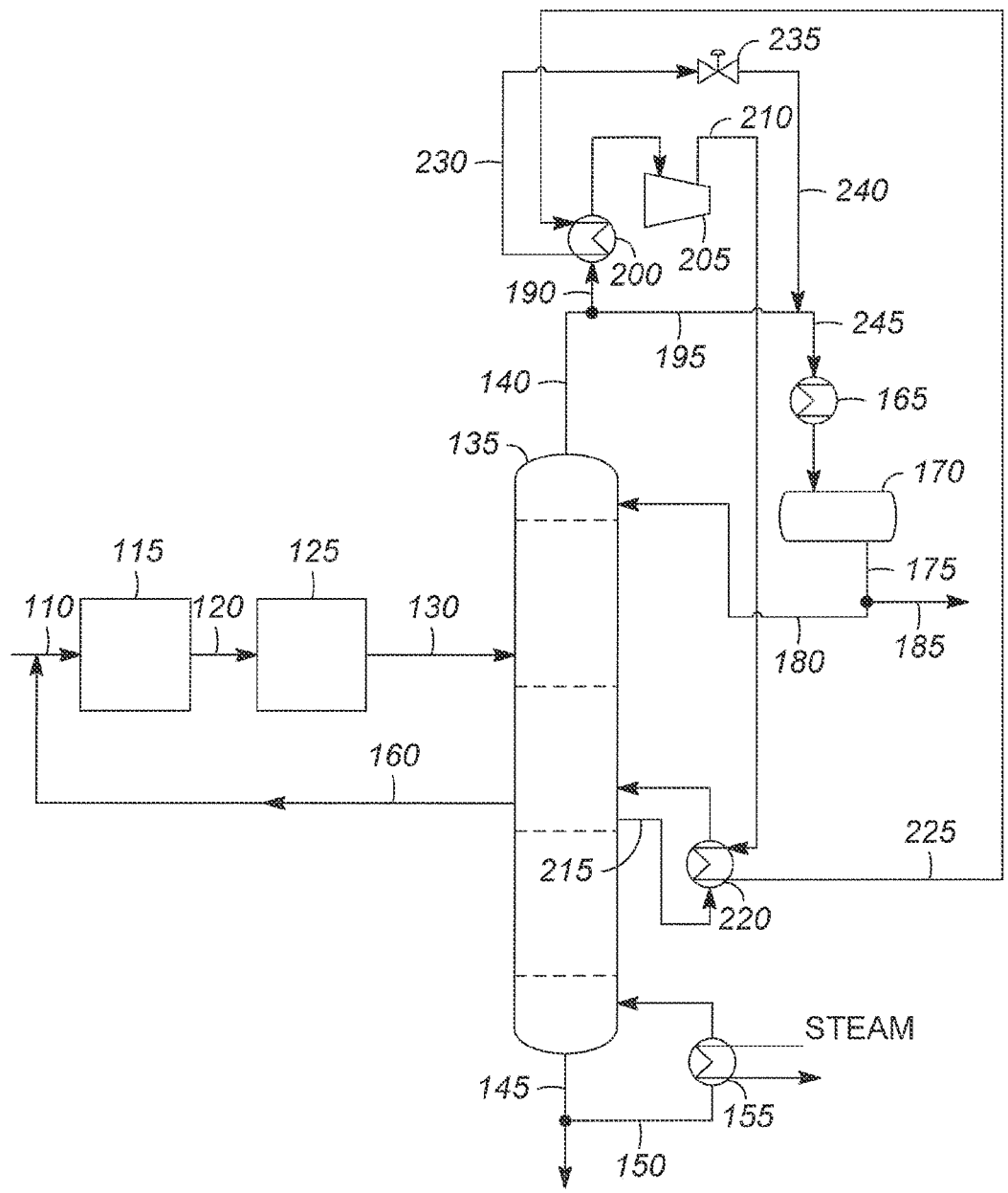
FIG. 2 is a schematic of one embodiment of a separation unit with a de-isohexanizer column having a heat pump.

FIG. 2 is an illustration of a heat pump used with a de-isohexanizer column (or other hydrocarbon distillation column). The feed 110 enters reactor 115, and the reactor effluent 120 is sent to stabilizer 125. The stabilizer bottoms stream 130 contains primarily $C_5$-$C_6$ hydrocarbons. By "contains primarily $C_5$-$C_6$ hydrocarbons," we mean that the feed stream is at least about 50 wt % $C_5$-$C_6$ hydrocarbons, or at least about 60 wt %, or at least about 70 wt %, or at least about 80 wt %, or at least about 85 wt %, or at least about 90 wt %.

The stabilizer bottoms stream 130 is separated in de-isohexanizer column 135 into an overhead stream 140 containing primarily di-methyl butane and lighter hydrocarbons, a bottoms stream 145 containing primarily $C_{7+}$ hydrocarbons and a side cut stream 160. By "containing primarily di-methyl butane and lighter hydrocarbons," we mean the overhead stream contains at least about 60 wt % di-methyl butane and lighter hydrocarbons, or at least about 70 wt %, or at least about 80 wt %, or at least about 90 wt %. By "containing primarily $C_{7+}$ hydrocarbons," we mean the bottoms stream contains about at least about 60 wt % $C_{7+}$ hydrocarbons, or at least about 70 wt %, or at least about 80 wt %, or at least about 90 wt %. A portion 150 of the bottoms stream 145 is sent to reboiler 155 where it is heated and returned to the de-isohexanizer column 135.

The side cut stream 160 is withdrawn from the de-isohexanizer column 135 and sent back to the reactor 110. The side cut stream 160 contains primarily methyl pentanes, normal hexane, and $C_6$ naphthenes. By "contains primarily methyl pentanes, normal hexane, and $C_6$ naphthenes," we mean that the side cut contains at least about 60 wt % methyl pentanes, normal hexane, and $C_6$ naphthenes, or at least about 70 wt %, or at least about 80 wt %, or at least about 85 wt %, or at least about 90 wt %. The side cut stream 160 is withdrawn at a position below the position where the stabilizer bottoms stream 130 enters the de-isohexanizer column 135.

The overhead stream 140 is divided into a first portion 190 and a second portion 195. The first portion 190 is sent through a heat exchanger 200 to increase the temperature to a temperature above the condensation temperature. It is then sent to the compressor 205 where it is compressed, increasing the temperature of the first portion 190.

A side stream 215 from the de-isohexanizer column 135 is sent to side reboiler 220. The side stream is heated in the side reboiler 220 using the compressed stream 210 from the compressor 205, and it is returned to the de-isohexanizer column 135 at a point above where it is taken out, but below the level of the side cut stream 160 (if present).

After contacting the side stream 215, the temperature of the compressed stream 210 is reduced. The compressed stream with the reduced temperature 225 is sent to heat exchanger 200. The reduced temperature compressed stream 225 has sufficient heat to superheat the first portion 190 of the overhead stream 140 prior to the first portion 190 entering the compressor 205. After superheating the first portion 190, the temperature of stream 230 is reduced further. Stream 230 goes through expansion valve 235 which reduces the pressure. Reduced pressure stream 240 (which has lower pressure than overhead stream 140) then joins with the second portion 195 of the overhead stream 140. The temperature of the combined stream 245 is reduced in heat exchanger 165, and sent to receiver 170. The outlet stream 175 from the receiver 170 is divided, with a first portion 180 being sent to the de-isohexanizer column 135 and the second portion 185 being recovered as an overhead product stream.

The term "portion" as used herein means a part of the stream, material, or object up to and including the entire stream, material, or object.

In another embodiment, the overhead stream 140 is not divided into first and second portions 190, 195, and the entire overhead stream 140 is treated in the manner described for the first portion 190.

In another embodiment, the reduced pressure stream 240 is not joined with the second portion 195 of the overhead stream 140 to form a combined stream.

In another embodiment, only a portion of side stream 215 is sent to side reboiler 220.

The use of the side reboiler reduces the temperature difference between the overhead stream and the stream used in the side reboiler (compared to the bottoms reboiler), which helps to improve the economics of the process. The temperature difference is desirably less than about 38.9° C. (70° F.), or less than about 27.7° C. (50° F.), or less than about 24.9° C. (45° F.), or less than about 22.2° C. (40° F.), or less than about 19.4° C. (35° F.), or less than about 16.6° C. (30° F.). For example, the temperature of the overhead stream 140 can be about 76° C. (169° F.) exiting the de-isohexanizer column, and the temperature of the side stream 215 before heating in the side reboiler 220 can be about 109° C. (229° F.).

If a side cut stream is used, the side reboiler stream will be returned to the de-isohexanizer column at a position determined by utilizing process modeling tools to optimize the heat pumped column design, as is known to those of skill in the art. The side reboiler stream can be returned to the column at a position above or below the position where the side cut stream is removed. In one embodiment, the optimum location was determined to be about two (2) theoretical trays below the position where the side cut stream is taken.

Suitable operating conditions for the de-isohexanizer column include a pressure between about 103 kPa-g (15 psig) and 262 kPa-g (38 psig) and an overhead temperature between about 65.5° C. (150° F.) and 85.0° C. (185° F.). The trayed column uses a bottoms reboiler which is usually heated by steam. The column is typically optimized based on the product octane required, and the operating conditions will vary based on this factor. Those of skill in the art would understand how to adjust the operating conditions to obtain the desired product octane.

Typical feed and product compositions for the column are provided in Table 1. The $C_5$ and di-methyl butanes are concentrated in the overhead stream, which has a reduced concentration of methyl pentanes. The $C_{7+}$ components are concentrated in the bottoms stream. The side draw includes high concentrations of methyl pentanes, normal $C_6$, and $C_6$ naphthenes, which can be recycled back to the reactor for further processing.

TABLE 1

| Component | Feed to Column (wt %) | Overhead liquid (wt %) | Bottoms (wt %) | Side Draw (wt %) |
|---|---|---|---|---|
| Butanes |  | 0.5 |  |  |
| C5 | 20.8 | 50.7 |  |  |
| DiMethyl-Butane | 21.8 | 41.4 |  | 9.2 |
| Methyl-Pentanes | 29.4 | 7.4 | 0.1 | 50.0 |
| n-C6 | 8.4 | 0.0 | 0.3 | 15.9 |
| C6 Naphthenes | 11.1 |  | 16.9 | 19.0 |
| C7+ | 8.5 |  | 82.7 | 5.9 |
| Total | 100.0 | 100.0 | 100.0 | 100.0 |

In another embodiment, the process can be used to separate a feed stream containing primarily $C_4$ hydrocarbons. By "containing primarily $C_4$ hydrocarbons," we mean that the feed stream is at least about 50 wt % $C_4$ hydrocarbons, or at least about 60 wt %, or at least about 70 wt %, or at least about 80 wt %, or at least about 85 wt %, or at least about 90 wt %, or at least about 95 wt %.

The feed stream can be separated in a de-isobutanizer column into an overhead stream containing primarily isobutane and lighter hydrocarbons, a bottoms stream containing primarily $C_{5+}$ hydrocarbons and a side cut stream. By "containing primarily isobutane and lighter hydrocarbons," we mean the overhead stream contains at least about 80 wt %, or at least about 85 wt %, or at least about 90 wt %, or at least about 92 wt %, or at least about 95 wt %, or at least about 98 wt %, or at least about 99 wt %. By "containing primarily $C_{5+}$ hydrocarbons," we mean the bottoms stream contains about at least about 60 wt % $C_{5+}$ hydrocarbons, or at least about 70 wt %, or at least about 80 wt %, or at least about 90 wt %, or at least about 95 wt %.

The side cut stream is withdrawn from the de-isobutanizer column and sent back to the reactor. The side cut stream contains primarily normal butanes. By "contains primarily normal butanes," we mean that the side cut contains at least about 60 wt % normal butanes, or at least about 70 wt %, or at least about 80 wt %, or at least about 85 wt %, or at least about 90 wt %, or at least about 95 wt %.

Typical feed and product compositions for an embodiment for separating butanes are provided in Table 2. The isobutane is concentrated in the overhead stream, while the normal butane is concentrated in the side draw. The $C_{5+}$ components are concentrated in the bottoms stream.

TABLE 2

| Component | Feed to Column (wt %) | Overhead liquid (wt %) | Bottoms (wt %) | Side Draw (wt %) |
|---|---|---|---|---|
| C3− | 0.02% | 0.04% | 0.00% | 0.00% |
| iC4 | 49.86% | 99.93% | 0.01% | 5.15% |

TABLE 2-continued

| Component | Feed to Column (wt %) | Overhead liquid (wt %) | Bottoms (wt %) | Side Draw (wt %) |
|---|---|---|---|---|
| nC4 | 46.97% | 0.03% | 14.09% | 93.55% |
| C5+ | 3.15% | 0.00% | 85.90% | 1.30% |
| Total | 100.00% | 100.00% | 100.00% | 100.00% |

Figure 3:
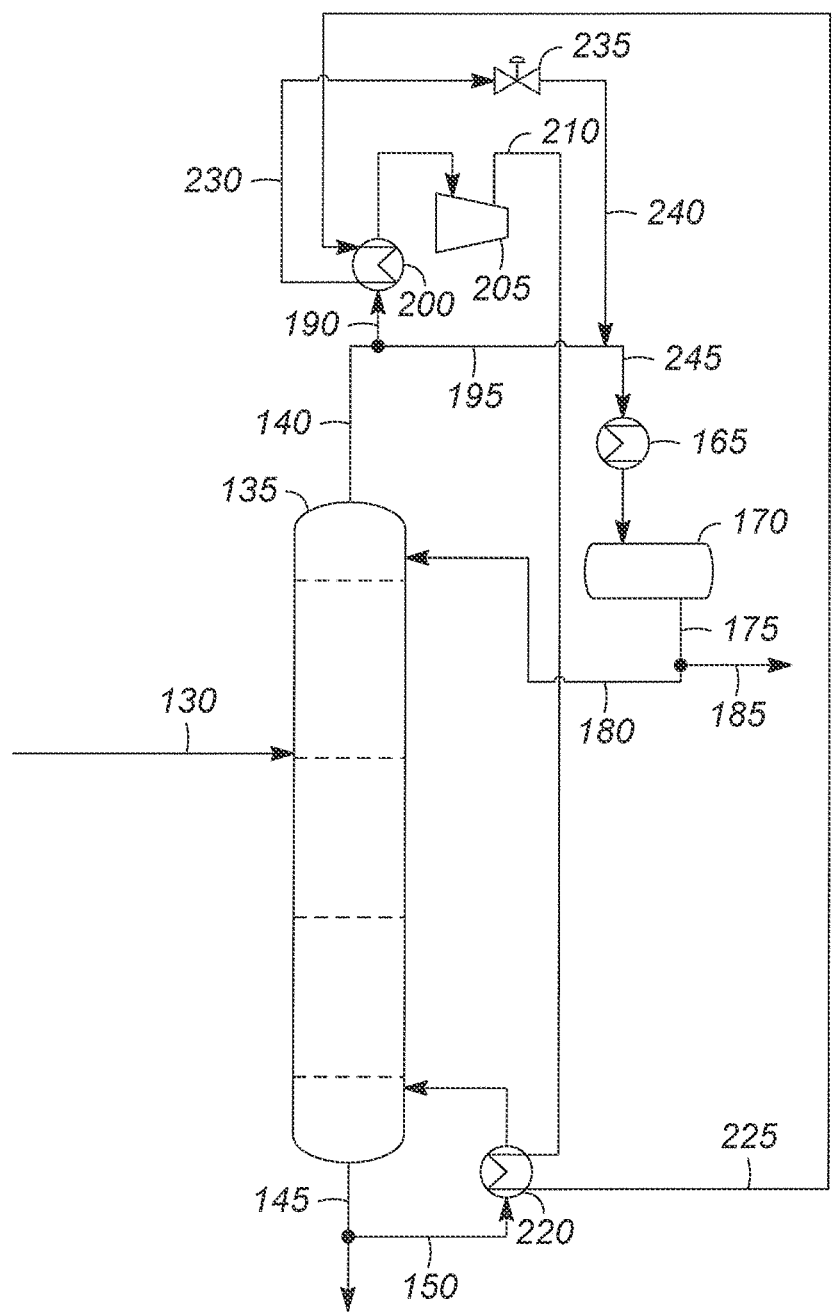
FIG. 3 is a schematic of another embodiment of a distillation column having a heat pump.

FIG. 3 shows another embodiment of a distillation column with a heat pump. This arrangement would be appropriate for a light hydrocarbon column with a narrower feed range, such as primarily $C_5$-$C_6$ hydrocarbons with little to no $C_{7+}$ hydrocarbons. By "primarily $C_5$-$C_6$ hydrocarbons with little to no $C_{7+}$ hydrocarbons," we mean that the feed stream is at least about 90 wt % $C_5$-$C_6$ hydrocarbons and less than about 2 wt % $C_{7+}$ hydrocarbons. The temperature difference between the overhead stream and the bottoms stream could be less than about 38.9° C. (70° F.). In this case, the side reboiler need not be used. Instead, the heat pump is used to heat the bottoms stream and a portion of the overhead stream before it goes to the compressor.

The feed stream 130 containing primarily $C_5$-$C_6$ hydrocarbons with little to no $C_{7+}$ hydrocarbons is separated in column 135 into an overhead stream 140 containing primarily di-methyl butane and lighter hydrocarbons and a bottoms stream 145 containing primarily methyl pentanes, normal hexane, and $C_6$ naphthenes.

The overhead stream 140 is divided into a first portion 190 and a second portion 195. The first portion 190 is sent through a heat exchanger 200 to increase the temperature to a temperature above the condensation temperature. It is then sent to the compressor 205 where it is compressed, increasing the temperature of the first portion 190.

A portion 150 of the bottoms stream 145 is sent to reboiler 220 where it is heated using the compressed stream 210 from the compressor 205, and it is returned to the column 135 at a point above where it is taken out.

After contacting the portion 150 of bottoms stream 145, the temperature of the compressed stream 210 is reduced. The compressed stream with the reduced temperature 225 is sent to heat exchanger 200. The reduced temperature compressed stream 225 has sufficient heat to superheat the first portion 190 of the overhead stream 140 prior to the first portion 190 entering the compressor 205. After superheating the first portion 190, the temperature of stream 230 is reduced further. Stream 230 goes through expansion valve 235 which reduces the pressure. Reduced pressure stream 240 then joins with the second portion 195 of the overhead stream 140. The temperature of the combined stream 245 is reduced in heat exchanger 165, and sent to receiver 170. The outlet stream 175 from the receiver 170 is divided, with a first portion 180 being sent to the column 135 and the second portion 185 being recovered as an overhead product stream.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A process for hydrocarbon distillation comprising:
   providing a hydrocarbon feed stream to a fractionation zone at a first position;

fractionating the hydrocarbon feed stream into an overhead stream and a bottoms stream;
heating a first portion of the overhead stream to a temperature above a dew point temperature of the overhead stream;
compressing the heated first overhead stream portion;
removing a portion of a stream from the fractionation zone at a second position below the first position;
heating the removed stream portion by indirectly contacting the removed stream portion with the compressed first overhead stream portion;
returning the heated removed stream portion to the fractionation zone at a third position above the second position and below the first position;
reducing the pressure of the compressed first overhead stream portion to form a reduced pressure overhead stream;
returning a portion of the reduced pressure overhead stream to the top of the fractionation zone;
wherein heating the first overhead stream portion comprises indirectly contacting the first overhead stream portion with the compressed first overhead stream portion after indirectly contacting the removed stream portion with the compressed first overhead stream portion and before reducing the pressure of the compressed first overhead stream portion.

2. The process of claim 1 wherein the removed stream portion is a side stream or the bottoms stream.

3. The process of claim 1 further comprising removing a side cut from the fractionation zone at a fourth position below the first position, the side cut having a boiling point between a boiling point of the overhead stream and a boiling point of the bottoms stream.

4. The process of claim 1 further comprising combining the reduced pressure overhead stream with a second overhead stream portion.

5. The process of claim 3 further comprising recycling the side cut to a reactor.

6. The process of claim 1 wherein indirectly contacting the removed stream portion with the compressed first overhead stream portion comprises heating the removed stream portion in a heat exchanger.

7. The process of claim 1 wherein a temperature difference between the overhead stream and the bottoms stream is at least about 38.9° C. (70° F.).

8. The process of claim 1 wherein the hydrocarbon feed stream contains primarily $C_5$-$C_6$ hydrocarbons, wherein the overhead stream contains primarily di-methyl butane and lighter hydrocarbons, and wherein the bottoms stream contains primarily $C_{7+}$ hydrocarbons.

9. The process of claim 8 wherein the removed stream portion is a side stream.

10. The process of claim 8 further comprising removing a side cut from the fractionation zone at a fourth position below the first position and above the third position, the side cut having a boiling point between a boiling point of the overhead stream and a boiling point of the bottoms stream, and wherein the side cut contains primarily methyl pentanes, normal hexane, and $C_6$ naphthenes.

11. The process of claim 1 wherein the hydrocarbon feed stream contains primarily $C_5$-$C_6$ hydrocarbons with little to no $C_{7+}$ hydrocarbons, wherein the overhead stream contains primarily di-methyl butane and lighter hydrocarbons, and wherein the bottoms stream contains primarily methyl pentanes, normal hexane, and $C_6$ naphthenes.

12. The process of claim 1 wherein the removed stream portion is a side stream and wherein a temperature difference between the removed stream portion before heating and the first portion of the overhead stream before heating is less than about 38.9° C. (70° F.).

13. The process of claim 1 further comprising providing additional heat to the first overhead stream portion during a start-up period using steam, and stopping the additional heat after the start-up period.

14. The process of claim 1 further comprising condensing the compressed first overhead stream portion or the reduced pressure overhead stream before returning the portion of the reduced pressure overhead stream to the top of the fractionation zone.

15. The process of claim 1 wherein the hydrocarbon feed stream contains primarily $C_4$ hydrocarbons, wherein the overhead stream contains primarily isobutane and lighter hydrocarbons, and wherein the bottoms stream contains primarily $C_{5+}$ hydrocarbons.

16. The process of claim 15 wherein the removed stream portion is a side stream.

17. The process of claim 15 further comprising removing a side cut from the fractionation zone at a fourth position below the first position and above the third position, the side cut having a boiling point between a boiling point of the overhead stream and a boiling point of the bottoms stream, and wherein the side cut contains primarily normal butanes.

* * * * *